United States Patent [19]

Husby et al.

[11] Patent Number: 5,310,685
[45] Date of Patent: May 10, 1994

[54] APPARATUS FOR DELIVERING A CALIBRATION STANDARD

[75] Inventors: Harry I. Husby, Milton; Robert D. Steinmeyer, Carrollton, both of Ky.

[73] Assignee: Dow Corning Corporation, Midland, Mich.

[21] Appl. No.: 939,322

[22] Filed: Sep. 2, 1992

[51] Int. Cl.⁵ .......................................... G01N 1/10
[52] U.S. Cl. .................................... 436/180; 422/100; 422/103; 141/130; 73/863.72; 73/863.73
[58] Field of Search .................... 422/100, 99, 103, 63; 436/180; 141/130, 1, 67; 73/863.71, 863.72, 863.73, 863.84, 864.85

[56] References Cited

U.S. PATENT DOCUMENTS

| | | | |
|---|---|---|---|
| 3,747,412 | 7/1973 | Jones | 73/863.72 |
| 4,009,618 | 3/1977 | Johnson | 73/863.84 |
| 4,574,850 | 3/1986 | Davis | 422/100 |
| 4,873,057 | 10/1989 | Robertson et al. | 436/180 |
| 4,887,473 | 12/1989 | Proni et al. | 73/864.35 |
| 5,256,573 | 10/1993 | Kuroda et al. | 436/179 |

OTHER PUBLICATIONS

Elmer, Gaden Jr., "Production Methods in Industrial Microbiology" 1981 p. 89.

*Primary Examiner*—James C. Housel
*Assistant Examiner*—Lien Tran
*Attorney, Agent, or Firm*—William F. Boley

[57] ABSTRACT

A sample delivery apparatus which can by used to repetitively deliver a sample to a process or an analyzer, either automatically or on demand. The sample delivery apparatus can be sealed under an inert atmosphere, thus minimizing the possibility of changes in the sample due to, for example, evaporation, hydrolysis, or oxidation. The design of the apparatus is such that only the volume of the actual sample delivered is consumed. Therefore, a large number of samples can be delivered with minimum consumption of the sample material. The sample delivery apparatus can be used to deliver both liquid and gaseous fluids. The present sample delivery apparatus is especially useful as an automated method for delivering a sample to calibrate on-line analyzers used to monitor chemical processes.

18 Claims, 2 Drawing Sheets

APPARATUS FOR DELIVERING A CALIBRATION STANDARD

BACKGROUND OF INVENTION

The present invention is a sample delivery apparatus which can by used to repetitively deliver a sample to a process or an analyzer, either automatically or on demand. The sample delivery apparatus can be sealed under an inert atmosphere, thus minimizing the possibility of changes in the calibration standard due to, for example evaporation, hydrolysis, or oxidation. The design of the apparatus is such that only the volume of the actual sample delivered is consumed. Therefore, a large number of samples can be delivered with minimum consumption of sample material. The sample delivery apparatus can he used to deliver both liquid and gaseous fluids. The present apparatus is especially useful as an automated method for delivering a sample to calibrate on-line analyzers used to monitor chemical processes. A variety of indirect and direct methods exist for calibrating on-line analyzers In a typical indirect method, a sample is periodically collected from the process stream, analyzed in a separate analyzer, and the on-line analyzer adjusted to agree with the off-line analysis. This method is subject to errors resulting for example, from compositional differences in the sample analyzed in the online analyzer and the sample analyzed in the off-line analyzer, from compositional changes in the sample collected for off-line analysis due to handling, and from random variation in both the off-line and on-line analysis.

The direct method of calibration avoids many of the sources of error incurred in the indirect method of calibration by introducing a prepared standard directly into the analyzer. Typically, direct calibration is done by flushing and filling the analyzer's sampling system with a calibration standard delivered from a pressurized reservoir. However, this procedure is wasteful since only a minor portion of the standard is used for calibration with the majority of the standard being consumed in flushing the sample system. An alternative direct calibration method involves injecting the calibration standard into the analyzer through an auxiliary septum-type inlet system by means of a syringe. Although syringe injection is less wasteful, it risks exposure of the calibration standard to the atmosphere, which can cause changes in composition when reactive materials are involved.

The biggest problem with the described calibration procedures is that they are manual in nature. As a result, they are time consuming and potentially hazardous. Consequently, the calibration of on-line analyzers have tended to be done infrequently and even when conducted the results are often inaccurate.

Therefore, an objective of the present invention is to provide an apparatus which can automatically and repetitively provide a sample of a material to an analyzer or a process. Another objective is to provide an apparatus which can be maintained under substantially inert conditions during multiple deliveries of a sample. Finally, it is an objective of the present invention to provide an apparatus which minimizes the total amount of sample required and essentially eliminates the loss of sample due to flushing of the cell used to deliver the sample.

SUMMARY OF INVENTION

The present invention is a sample delivery apparatus which can by used to repetitively deliver a sample to a process or an analyzer, either automatically or on demand. The sample delivery apparatus can be sealed under an inert atmosphere, thus minimizing the possibility of changes in the sample due to, for example, evaporation, hydrolysis, or oxidation. The design of the apparatus is such that only the volume of the actual sample delivered is consumed. Therefore, a large number of samples can be delivered with minimum consumption of the sample material. The sample delivery apparatus can be used to deliver both liquid and gaseous fluids. The present sample delivery apparatus is especially useful as an automated method for delivering a sample to calibrate on-line analyzers used to monitor chemical processes.

DESCRIPTION OF INVENTION

The present invention is an apparatus for repetitively delivering a quantity of fluid from a reservoir into a flowing gas or liquid stream. The apparatus is especially suitable for the automated delivery of a reference standard to an on-line analyzer used to monitor a chemical process. In one embodiment, the apparatus comprises, a pump separated into a pressure chamber and a sample chamber by an expandable means, the sample chamber connected to a first reservoir, the first reservoir connected through a sample changer containing a positionable sample well to a second reservoir, where the pressure chamber, the first reservoir, the sample changer, and the second reservoir form a pressurizable apparatus and the positionable sample well has a first position within the sample chamber which permits fluid transfer between the first reservoir and the second reservoir and a second position within the sample changer which permits transfer of fluid contained in the positionable sample well to be removed from the apparatus. The first reservoir is optional and in another embodiment of the present invention the apparatus can be operated without the presence of the first reservoir.

Figure 1A:
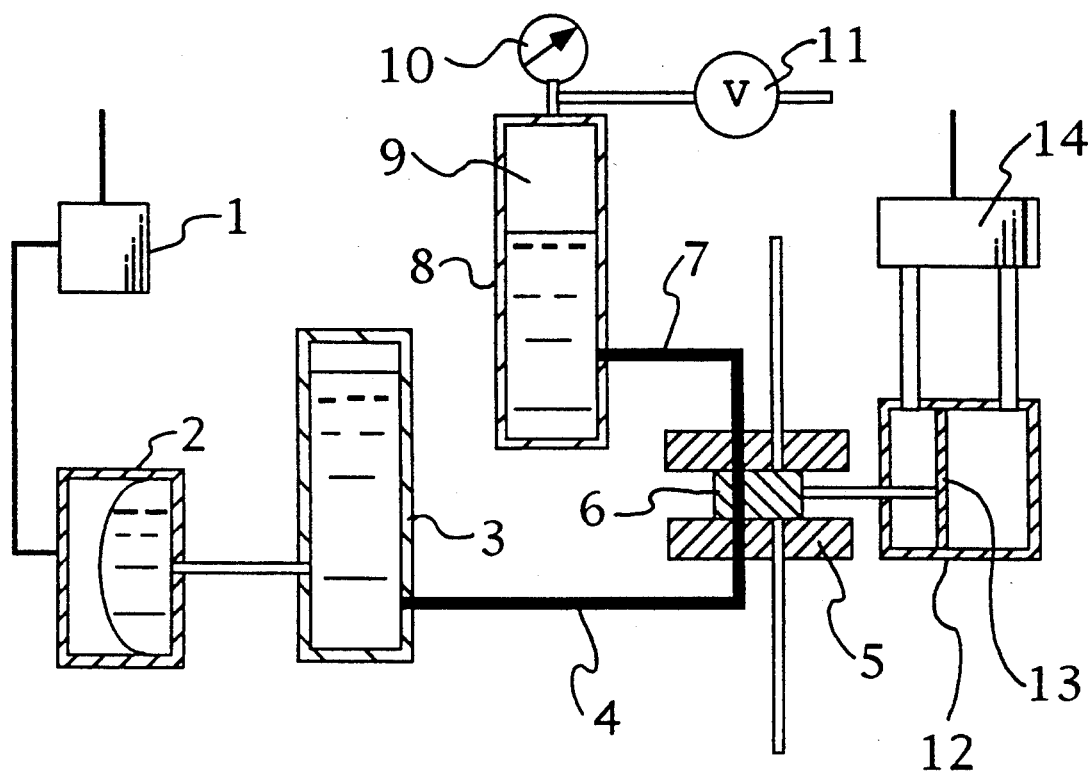
FIGS. 1a, 1b, and 1c are schematic representations of operating configurations of an embodiment of the present invention using a diaphragm for flushing and filling a sample delivery cell.
Figure 1B:
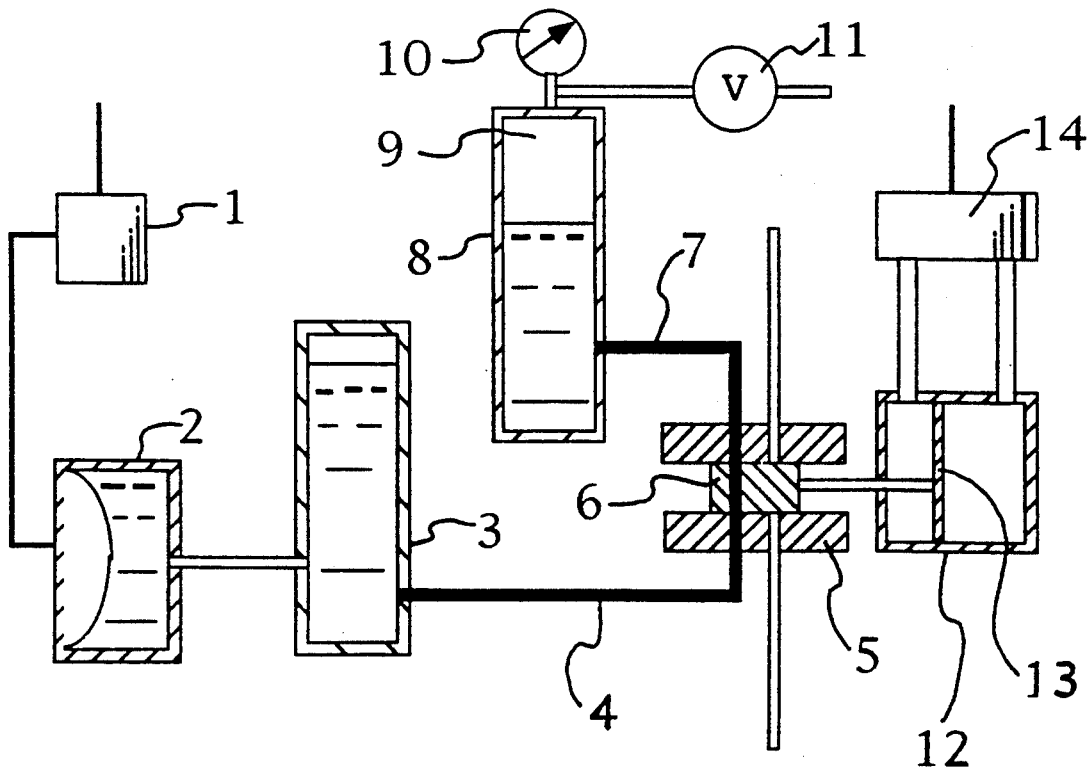
Figure 1C:
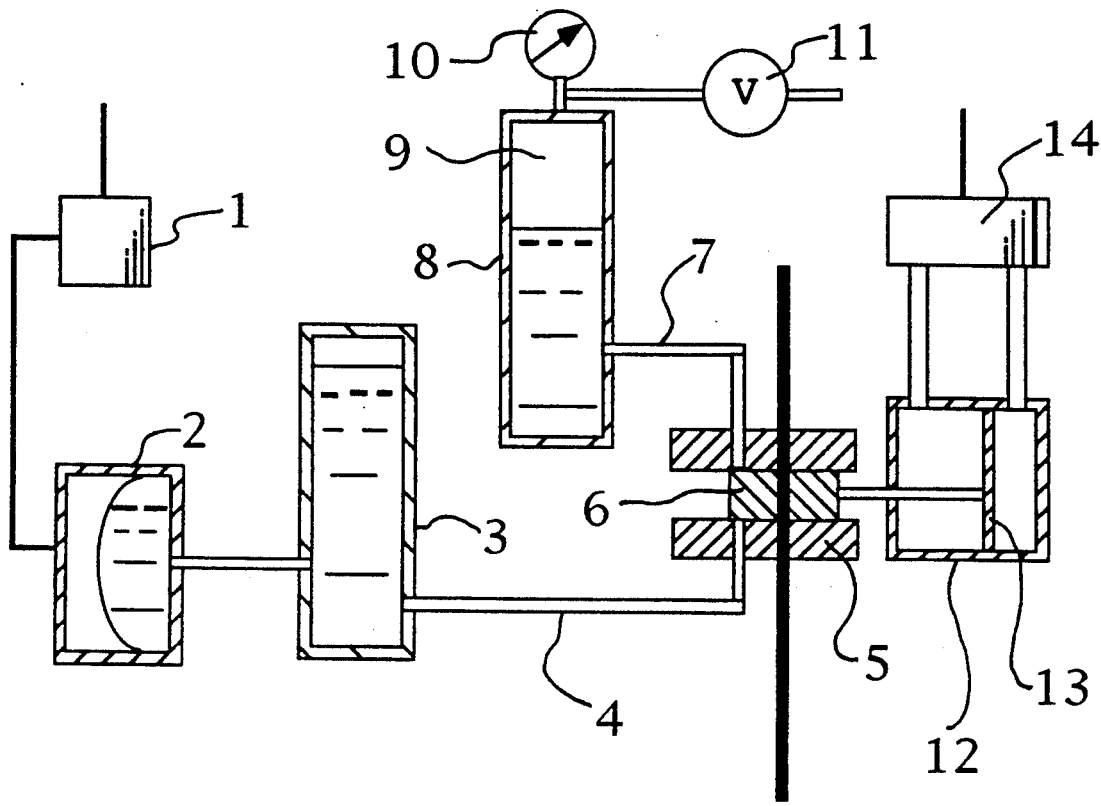

FIGS. 1a, 1b, and 1c demonstrate a useful configuration of the present sample delivery apparatus and the mode of operation. FIG. 1a demonstrates a configuration of the present sample delivery apparatus in a mode for flushing and filling a well in a sample chamber. The flushing and filling process is demonstrated in FIG. 1b. The sample delivery apparatus comprises solenoid activator 1, which provides pressure to pump 2 causing inversion, expansion, or both of a diaphragm which separates the pump into a pressure chamber and a sample chamber. Pressure to the diaphragm of pump 2 forces sample from the pump sample chamber into reservoir 3. Those skilled in the art will recognize that reservoir 3 serves to increase the overall volume of sample contained within the apparatus. Reservoir 3 is optional and can be omitted from the system if the additional volume is not required. The resultant increase in pressure in reservoir 3 causes sample to flow through conduit 4 to sample valve 5. Within sample valve 5, positionable sample well 6 is located to created an open conduit between reservoir 3 and reservoir 8. A pressure differential between reservoir 3 and reservoir 8 causes sample to flow through positionable sample chamber 6 to flush the well. Any residual carrier material in positionable sample well 6 is flushed into reservoir 8. The flushed carrier material is diluted in the much larger volume of reservoir 8 and thus has no significant effect on the sample material to be delivered. When the material to be transferred is a liquid, reservoir 8 has head space 9 which contains an inert gas at a lower pressure than that created in the apparatus by pump 2. The pressure in head space 9 is monitored by gage 10 and controlled through valve 11. The pressure in head space 9 acts as a spring forcing sample back through the apparatus when pressure is released on pump 2. Therefore to fill positionable sample well 6, solenoid activator 1 is deactivated to reduce the pressure in the apparatus and the pressure in head space 9 forces sample back through the apparatus.

In FIG. 1c, positionable sample well 6 has been positioned within sample valve 5 to provide for delivery of a sample contained within positional sample well 6. Positionable sample well 6 is connected to piston 13 located within positioner 12. Positioner 12 is connected to solenoid activator 14 which controls gas pressure on piston 13 to effects its position within positioner 12, and consequently the position of positionable sample well 6.

When positionable sample well 6 is in the position shown in FIG. 1c, the sample can be removed from the well by a suitable carrier gas or carrier liquid and delivered to an on-line analyzer or a process. After the sample is removed from positionable sample well 6, the apparatus can be returned to the configuration shown in FIG. 1a and the flushing, filling, and delivery process performed repetitively.

Figure 2:
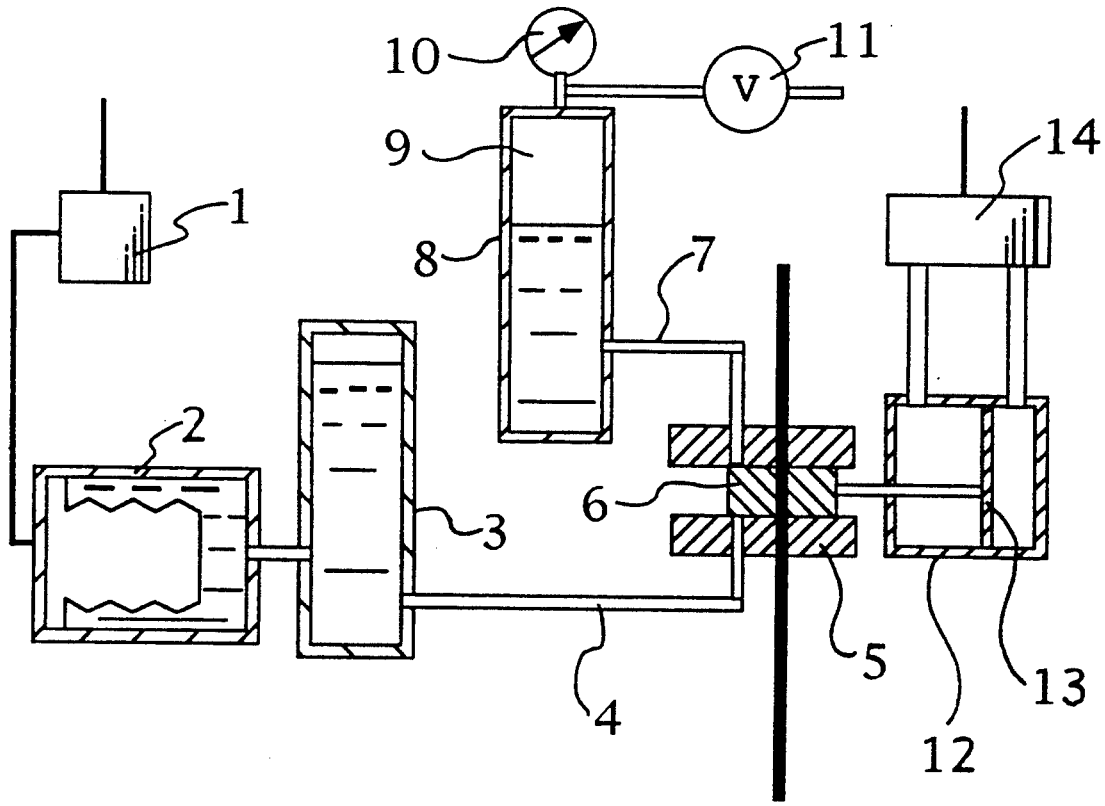
FIG. 2 is a schematic representation of an embodiment of the present invention using a bellow for flushing and filling a sample delivery cell.

FIG. 2 shows an apparatus in which the expandable means within pump 2 is a bellows. The remainder of the apparatus configuration and the operation of the FIG. 2 apparatus is similar to that described for FIGS. 1a, 1b, and 1c.

Those skilled in the art will recognize that solenoid activator 1 and solenoid activator 14 can be any standard device suitable for controlling delivery of a pressurized gas or liquid and can be manually controlled or controlled by standard automation procedures. A preferred mode of operation of the present sample delivery apparatus is where the solenoid activators are automatically controlled to provide periodic standardization samples to an on-line analyzer. Although the pressure actuation of pump 2 and positioner 12 by gas is a preferred method, the pump and positioner can also be actuated by a pressurized fluid or other suitable means, for example, a mechanical means such as a motor.

Suitable materials of construction for the present apparatus will depend upon the fluid to be delivered by the apparatus. Generally, any material that does not unacceptably react with the fluid to be delivered and possesses the necessary physical strength is acceptable. The pump housing, the reservoirs, the sample valve, and the positionable sample well can be fabricated from for example, inconel, hastelloy, stainless steel, and teflon. The conduits used to connect the various components of the apparatus can be fabricated from, for example, inconel, hastelloy, stainless steel, or teflon The diaphragm within pump 2 can be constructed from, for example, a flexible polymeric material such as polyurethane, polypropylene, polycarbonate, or teflon. If a bellow is employed in pump 2, the bellow can be fabricated from a flexible polymeric material as previously described or a flexible metal material.

The gas used to pressurize pressure head space 9 of reservoir 8 can be any gas which is inert to the liquid or gas-sample contained within the sample delivery apparatus for delivery. For most applications, a suitable inert gas has been found to be nitrogen gas or helium gas. A suitable pressure for the gas in head space 9 is within a range having a lower value sufficient to force sample through the apparatus when pressure is released on pump 2 and a high value less than the pressure exerted within the apparatus by pump 2. Generally, a pressure within a range of about 1 psig to 30 psig is considered useable. Higher pressures may be used but to no perceived advantage.

Sample valve 5 can be of any standard design for capturing a sample from a flowing stream and transferring the captured sample to a second flowing stream. Sample valve 5 can be, for example, of a sliding design or of a rotating design.

The following operating examples are offered to facilitate understanding of the present invention. These examples are not intended to limit the claims herein.

Example 1. An apparatus similar to that illustrated in FIG. 1a and operated as previously described was employed.

Humphries solenoid activators (Model 41El, Kalamazoo, Mich.) were used to actuate the diaphragm of the pump and to control the positioning of the positionable sample well. The solenoid activators were installed on and controlled by an automated gas chromatograph (model MS IV, Fluid Data-Amscor, Angleton, Tex.). All conduits were teflon tubing. The two reservoirs were fabricated from teflon and each had a volume of about 100 mL. The sample valve was purchased from Fluid Data-Amscor and the positionable sample well within the sample valve had a volume capacity of about 0.25 microliters. Reservoir 2 contained a gas pressure head of about 5 psig using helium gas as the pressurizing gas.

The sample delivery apparatus was filled with of 0.001 Normal HCl in isopropyl alcohol (IPA) The sample valve was installed upstream of a detector cell in the solvent line of an electrolytic conductivity detector (ECD) system. The reservoir of the ECD system was filled with IPA. which served as a carrier to sweep the HCl standard from the positionable sample well through the ECD. The ECD electronics module was connected to a strip chart adjusted to gave a sensitivity of about a 10 percent scale deflection in response to a 0.25 microliter injection of the HCl standard.

About 1 mL of the HCl standard was used to automatically flush the positionable sample well prior to each filling. The apparatus was operated to automatically deliver a sample of the standard to the ECD system every 20 minutes for 5 days for a total of 357 samples. The mean response for the strip chart deflection was 10.6 with a standard deviation of 0.51.

Example 2. An apparatus similar to that described in Example 1 was employed with the exception that the pump used a metal bellows as the expandable means. The cleaned sample delivery apparatus was purged with dry helium and filled with a mixture of chlorosilanes containing about six percent n-octane as an internal standard. An automatic timer was programed to initiate an analysis of the mixture at about three hour intervals, for a total of 861, samples over a period of about four months. Helium gas was used as a carrier to transport the sample to a gas chromatograph using a thermal conductivity detector (GLC-TC). The results are presented in Table 1 as the weight percent composition for each chlorosilane. The standard deviation (Std. Dev.) in the weight percent for each chlorosilane is also presented.

TABLE 1

Variation in Repetitive Analysis For Chlorosilanes

| Chlorosilane | GLC-TC Weight % | | | |
|---|---|---|---|---|
| | $MeHSiCl_2$ | $Me_3SiCl$ | $MeSiCl_3$ | $Me_2SiCl_2$ |
| Mean | 3.72 | 2.54 | 6.98 | 86.47 |
| Std. Dev. | 0.11 | 0.14 | 0.11 | 2.45 |

We claim:

1. A sample delivery apparatus comprising: a pump separated into a pressure chamber and a sample chamber by an expandable means, the sample chamber connected through a sample valve having a positionable sample well to a reservoir; where the sample chamber, the sample valve, and the reservoir form a closed pressurizable system containing a fluid sample and means for pressurizing said system and the positionable sample well has a first position within the sample valve which permits fluid transfer between the sample chamber ant the reservoir and a second position within the sample valve which permits fluid contained in the positionable sample well to be removed from the sample delivery apparatus.

2. A sample delivery apparatus according to claim 1, where the expandable means is a diaphragm.

3. A sample delivery apparatus according to claim 1, where the expandable means is a bellows.

4. A sample delivery apparatus comprising: a pump separated into a pressure chamber and a sample chamber by an expandable means, the sample chamber connected to a first reservoir, the first reservoir connected through a sample valve having a positionable sample well to a second reservoir; where the sample chamber, the first reservoir, the sample valve, and the second reservoir for a closed pressurizable system containing a fluid sample and means for pressurizing said system and the positionable sample well has a first position within the sample valve which permits fluid transfer between the first reservoir and the second reservoir and a second position within the sample valve which permits fluid in the positionable sample well to be removed from the sample delivery apparatus.

5. A sample delivery apparatus according to claim 4, where the expandable means is a diaphragm.

6. A sample delivery apparatus according to claim 4, where the expandable means is a bellows.

7. A procedure for delivering a sample from a closed pressurized system comprising the steps of:
   (A) actuating an expandable means of a pump to separate said pump into a pressure chamber and a sample chamber, thereby forcing the sample from the sample chamber to a sample valve, said valve having a positionable sample well positioned to allow the sample to flow from said valve into a closed reservoir thereby increasing a pressure in the reservoir,
   (B) releasing actuation of the expandable means, thereby allowing the pressure in the reservoir to effect flow of the sample from the reservoir through the sample valve to the sample chamber of the pump,
   (C) positioning the positionable sample well within the sample valve to deliver the sample contained within the positionable well,
   (D) flushing the sample from the positionable well by means of a carrier gas or liquid, and
   (E) repeating steps A through D.

8. A procedure according to claim 7, where the expandable means is a diaphragm.

9. A procedure according to claim 7, where the expandable means is a bellows.

10. A procedure according to claim 7, where the reservoir is pressurized with an inert gas.

11. A procedure according to claim 7, where the sample is a chlorosilane.

12. A procedure according to claim 7, where actuation of the expandable means and positioning of the positionable sample well is automatically controlled.

13. A procedure for delivering a sample from a closed pressurizable system comprising the steps of:
   (A) actuating an expandable means of a pump to separate said pump into a pressure chamber and a sample chamber, thereby forcing the sample from the sample chamber into a first closed reservoir then from the first reservoir to a sample valve, said valve having a positionable sample well positioned to allow the sample from said valve to flow into a second closed reservoir thereby increasing a pressure in the second reservoir,
   (B) releasing actuation of the expandable means, thereby allowing the pressure in the second reservoir to effect flow of the sample form the second reservoir through the sample valve tot he first reservoir,
   (C) positioning the positionable sample well within the sample valve to deliver the sample contained within the positionable sample well,
   (D) flushing the sample form the positionable sample well by means of a carrier gas or liquid, and
   (E) repeating steps A through D.

14. A procedure according to claim 13, where the expandable means is a diaphragm.

15. A procedure according to claim 13 where the expandable means is a bellows.

16. A procedure according to claim 13, where the second reservoir is pressurized with an inert gas.

17. A procedure according to claim 13, where the sample is chlorosilanes.

18. A procedure according to claim 13, where actuation of the expandable means and positioning of the positionable sample well is automatically controlled.

* * * * *